United States Patent [19]

Hirao et al.

[11] Patent Number: 5,224,138
[45] Date of Patent: Jun. 29, 1993

[54] SLIP RING DEVICE

[75] Inventors: Yoshiki Hirao; Kozi Natori; Koki Kikuchi, all of Tochigi, Japan

[73] Assignee: Kabushiki Kaisha Toshiba, Kawasaki, Japan

[21] Appl. No.: 826,596

[22] Filed: Jan. 28, 1992

[30] Foreign Application Priority Data

Jan. 28, 1991 [JP] Japan .................................... 3-25075

[51] Int. Cl.$^5$ .......................................... H01R 39/08
[52] U.S. Cl. .......................................... 378/15; 378/4; 310/232; 310/235
[58] Field of Search ........................ 378/4, 15, 91, 101; 310/232, 235, 248, 249

[56] References Cited

U.S. PATENT DOCUMENTS

| | | | |
|---|---|---|---|
| 4,403,164 | 9/1983 | Preece | 310/232 |
| 5,018,174 | 5/1991 | Collins | 310/232 |
| 5,054,189 | 10/1991 | Bowman et al. | 310/232 |

Primary Examiner—David P. Porta
Attorney, Agent, or Firm—Finnegan, Henderson, Farabow, Garrett & Dunner

[57] ABSTRACT

A slip ring device comprises a cylindrical body of an insulating material, at least one ring of an electrically conductive material fitted on the outer periphery of the cylindrical body, at least one strip member of an electrically conductive material arranged on the outer periphery of the ring, a coupling member, situated between the strip member and the outer periphery of the ring, for electrically coupling the strip member and the outer periphery of the ring, at least one lead member of an electrically conductive material, having one end portion electrically connected to the ring and the other end portion led out of the inner periphery of the cylindrical body, and a brush unit of an electrically conductive material, situated in electrical contact with the strip member.

21 Claims, 6 Drawing Sheets

SLIP RING DEVICE

BACKGROUND OF THE INVENTION

1. Field of the Invention

The present invention relates to a slip ring device for transmitting electric power or electric signals between a stator and a rotor of a rotary electric machine.

2. Description of the Related Art

A typical rotary electric machine is a electric power apparatus such as an electric motor or a generator, or a medical treatment apparatus such as an x-ray CT scanner. This type of rotary electric machine comprises a stator and a rotor. In general, the stator and rotor are provided with a slip ring device. The slip ring device functions to transmit electric signals or electric power between the stator and rotor.

Figure 1:
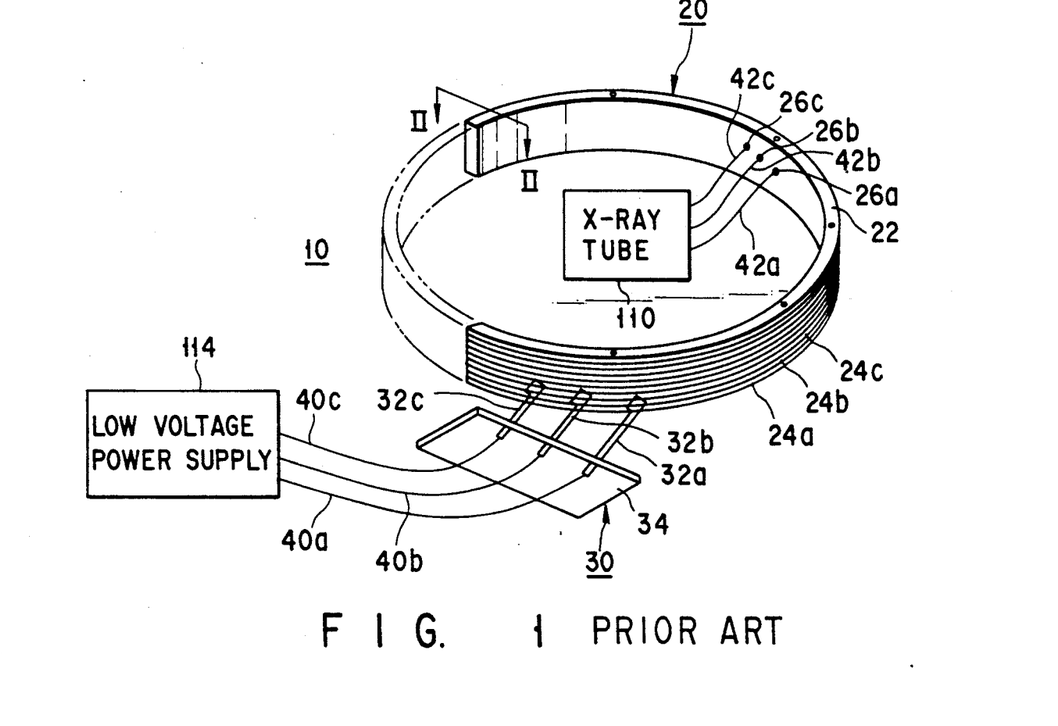
FIG. 1 is a perspective view showing an example of a conventional slip ring device mounted in an x-ray CT scanner.

A conventional slip ring device mounted in an x-ray CT scanner will now be described with reference to FIGS. 1 and 2. As is shown in FIG. 1, a slip ring device 10 comprises a cylindrical body 20 mounted on a rotor (not shown), and a brush unit 30 constituted by an n-number of brushes 32 and a block 34 mounted on a stator (not shown). In the following description, the n-number of brushes 32 are represented by three brushes 32a, 32b and 32c.

An x-ray tube 110 is fixed to the rotor (not shown). Accordingly, the x-ray tube 110 and the cylindrical body 20 rotate as one body. The cylindrical body 20, as shown in FIG. 2, includes an insulating resin cylindrical member 22, and an n-number of metal rings 24 arranged in parallel on the outer periphery of the cylindrical member 22 and distanced from one another. In the following description, the n-number of metal rings 24 are represented by three metal rings 24a, 24b and 24c.

The brushes 32a, 32b and 32c are always put in contact with the metal rings 24a, 24b and 24c during rotation of the cylindrical body 20. The brushes 32a, 32b and 32c are attached to the block 34. The block 34 is connected to a low voltage power supply 114 via an n-number of cables 40. In the following description, the n-number of cables 40 are represented by three cables 40a, 40b and 40c.

Figure 2:
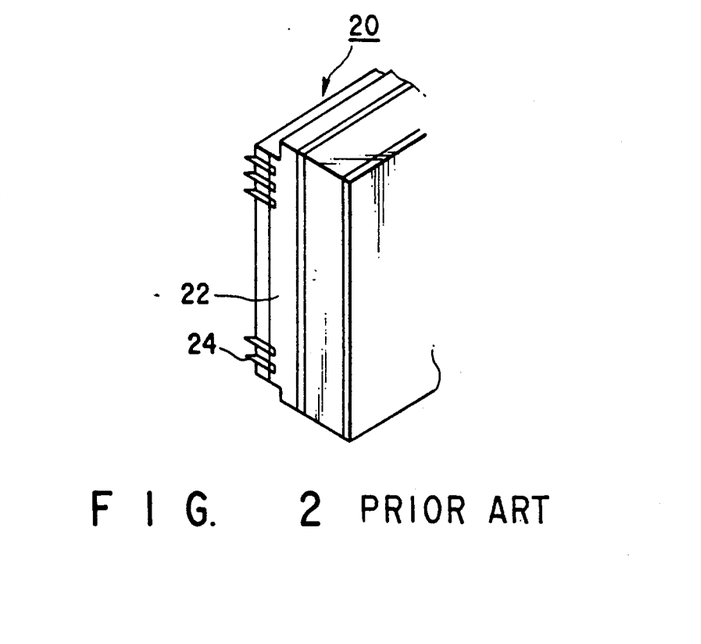
FIG. 2 is a cross-sectional view taken along line II—II in FIG. 1.

An n-number of electrically conductive screws 26 are penetrated from the metal rings 24a, 24b and 24c through the insulating resin cylindrical member 22, as shown in FIG. 2. In the following description, the n-number of screws 26 are represented by three electrically conductive screws 26a, 26b and 26c. First end portions of an n-number of cables 42 are connected to the tip end portions of the screws 26a, 26b and 26c. Second end portions of the cables 42 are connected to the x-ray tube 110. In the following description, the n-number of cables 42 are represented by three cables 42a, 42b and 42c.

With the above structure, even when the cylindrical body 20 and the x-ray tube 110 are rotated, electric power can easily be supplied from the low voltage power supply 114 to the x-ray tube 110 through the cables 40a, 40b and 40c, block 34, brushes 32a, 32b and 32c, metal rings 24a, 24b and 24c, electrically conductive screws 26a, 26b and 26c, and cables 42a, 42b and 42c.

In order to ensure good electrical connection between the low voltage power supply 114 and x-ray tube 110, as stated above, it is necessary to enhance electrical characteristics of the cylindrical body 20. In addition since the cylindrical body 20 is continuously rotated, wear resistance of the cylindrical body 20 must be increased.

To solve this problem, a silver plating has conventionally been applied to the metal rings 24a, 24b and 24c, or metal rings 24a, 24b and 24c made of a silver-based alloy have been employed.

The silver plating, however, incurs pollution problems, and, if the diameter of the silver-plated cylindrical body 20 is increased by the plating layer, the manufacturing cost increases.

SUMMARY OF THE INVENTION

The object of the present invention is to provide a slip ring device having good electrical connection and wear resistance, resulting in low manufacturing cost.

This object can be achieved by a slip ring device comprising:

a cylindrical body of an insulating material;

at least one ring of an electrically conductive material fitted on the outer periphery of the cylindrical body;

at least one strip member of an electrically conductive material arranged on the outer periphery of the ring;

coupling means, situated between the strip member and the outer periphery of the ring, for electrically coupling the strip member and the outer periphery of the ring;

at least one lead member of a electrically conductive material, having one end portion electrically connected to the ring and the other end portion led out of the inner periphery of the cylindrical body; and a brush unit of an electrically conductive material, situated in electrical contact with the strip member.

In addition, the object can be achieved by a slip ring device comprising:

a cylindrical body of an insulating material;

at least one ring of an electrically conductive material fitted on the outer periphery of the cylindrical body;

at least one strip member of an electrically conductive material arranged on the outer periphery of the ring;

at least one lead member of an electrically conductive material, having one end portion electrically connected to the ring and the other end portion led out of the inner periphery of the cylindrical body; and a brush unit of an electrically conductive material, situated in electrical contact with the strip member.

Furthermore, the object can be achieved by a slip ring device comprising:

a cylindrical body of an insulating material;

at least one strip member of an electrically conductive material arranged on the outer periphery of the cylindrical body;

at least one lead member of an electrically conductive material, having one end portion electrically connected to the strip member and the other end portion led out of the inner periphery of the cylindrical body; and a brush unit of an electrically conductive material, situated in electrical contact with the strip member.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIGS. 11, 12 and 13 show a slip ring device according to a fourth embodiment of the invention mounted in an x-ray CT scanner, wherein

DETAILED DESCRIPTION OF THE PREFERRED EMBODIMENTS

Figure 3:
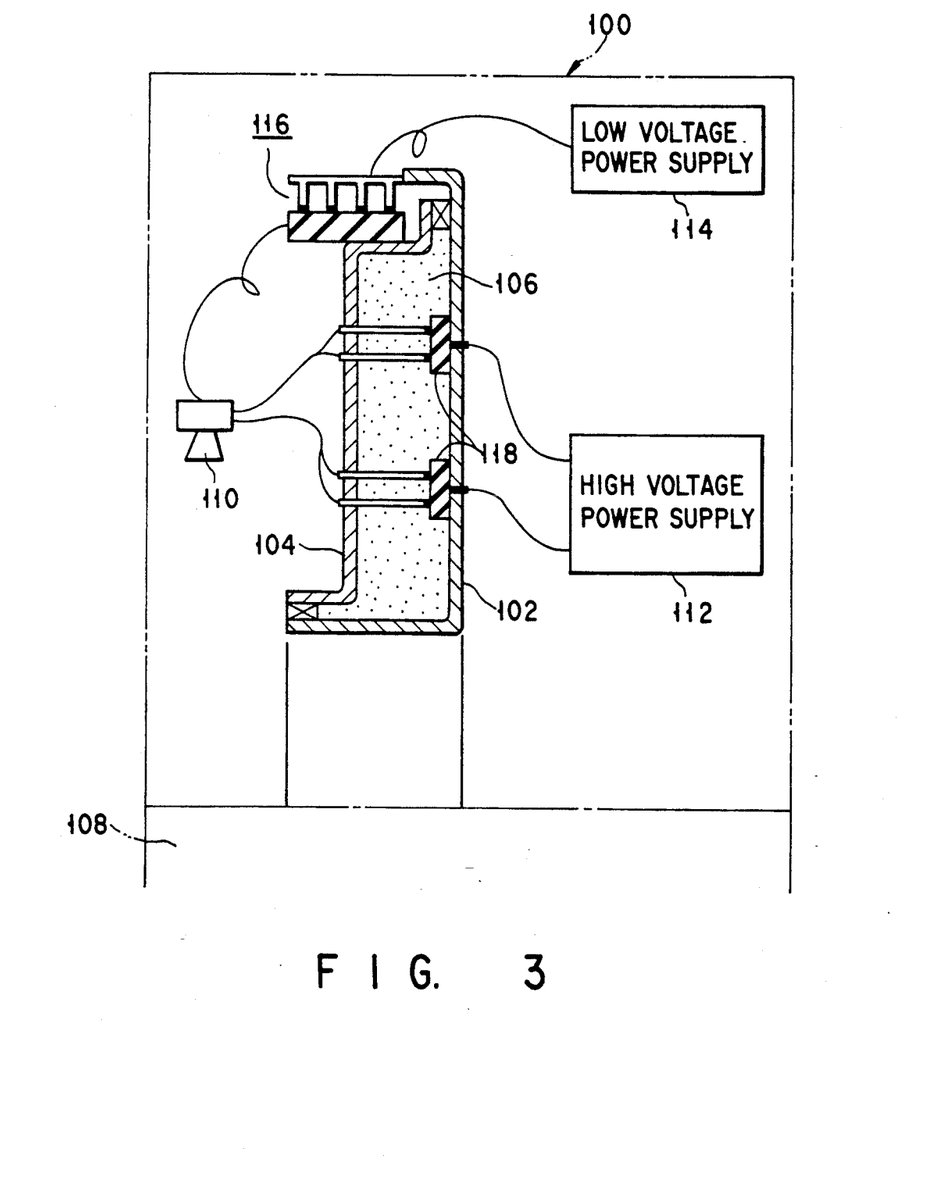
FIG. 3 is a cross-sectional view showing an important portion of an x-ray CT scanner.

A slip ring device according to the present invention, which has been applied to an x-ray CT scanner, will now be described. As is shown in FIG. 3, in an x-ray CT scanner, a stator 102 is arranged within a gantry 100. The stator 102 and a rotor 104 constitute a closed space 106. A subject-insertion hole 108 is formed at a center part of the rotor 104. An x-ray tube 110 and an x-ray detector (not shown) are arranged so as to interpose the hole 108 therebetween. The x-ray tube 110 and the x-ray detector are rotated relative to a subject (not shown), and x-rays are radiated from the x-ray tube 110 on to one side of the subject; thus, the x-ray detector can obtain x-ray transmission information from the other side of the subject. The x-ray transmission information is signal-processed by a signal processing system (not shown), thereby reconstructing a tomogram.

In general, in a third-generation x-ray CT scanner, both x-ray tube 110 and x-ray detector are installed in the rotor 104. The x-ray detector is an arcuated multichannel detector. In a forth-generation x-ray CT scanner the x-ray tube 110 is installed in the rotor 104, and the x-ray detector, which is an annular multichannel detector, is installed in the stator 102.

The x-ray tube 110 has an anode and a cathode. A high voltage is supplied from a high voltage power supply 112 to the anode, and a filament current is supplied from a lower voltage power source to the cathode. Since the high voltage power supply 112 and low voltage power supply 114 are installed in the stator 102 or stationary part (floor), a high voltage from the high voltage power supply 112 or filament current from the low voltage power supply 114 must be supplied from the stator to the rotor side via transmission means. An example of the transmission means is a slip ring device.

The x-ray detector has a bias electrode and a signal electrode. In a third-generation x-ray CT scanner, the x-ray detector is installed in the rotor 104. In addition to the x-ray detector, a signal collector (not shown) constituted mainly by an A/D converter is installed in the rotor 104. The x-ray detector and signal collector are supplied with control voltage from the low voltage power supply 114. An electric signal proportional to the quantity of incident x-rays is obtained from the x-ray detector and signal collector. Since the low voltage power supply 114 is installed in the stator 102 or stationary part (floor), the control voltage from the low voltage power supply 114 must be supplied from the stator 102 to the rotor side via transmission means. The electric signal must be input to the signal processing system. Since the signal processing system is installed in the stator 102 or stationary part (floor), the electric signal from the x-ray detector and signal collector must be supplied from the rotor 104 to the stator side via transmission means. An example of this transmission means is a slip ring device.

In general, the slip ring device is classified into a low voltage slip ring device and a high voltage slip ring device. The x-ray CT scanner shown in FIG. 3 is assumed to be a forth-generation x-ray CT scanner. As is shown in FIG. 3, the forth-generation x-ray CT scanner according to the present embodiment comprises a low voltage slip ring device 116 situated in the outside atmosphere, and a high voltage slip ring device arranged within a closed space 106 in which an insulating gas such as $SF_6$ is sealed. The x-ray CT scanner comprises these two types of slip ring devices 116 and 118 because it must treat greatly different voltages.

Figures 4, 6:
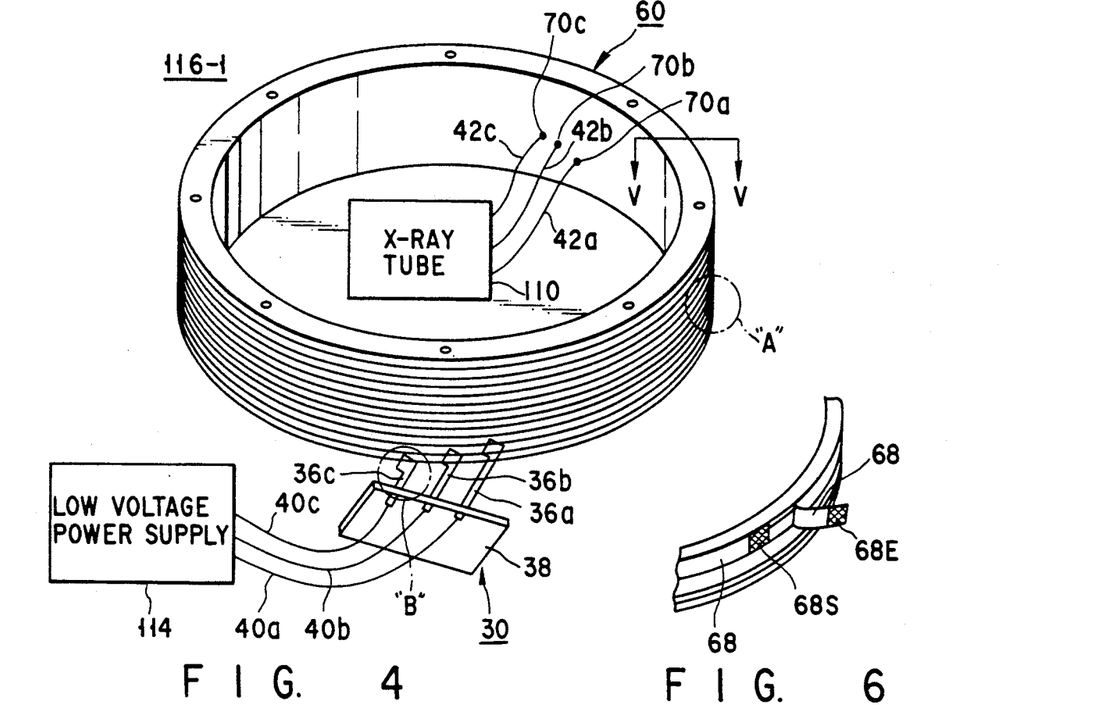
FIG. 4 is a perspective view showing a slip ring device according to a first embodiment of the present invention mounted in an x-ray CT scanner.
FIG. 6 is a partial perspective view showing portion A in FIG. 4 in detail.

FIG. 4 is a perspective view showing a low voltage slip ring device 116-1 according to a first embodiment of the present invention. As is shown in FIG. 4, the slip ring device 116-1 comprises a cylindrical body 60 mounted on a rotor (not shown) and a brush unit 30 mounted on a stator (not shown). An x-ray tube 110 is fixed to the rotor. Accordingly, the x-ray tube 110 and the cylindrical body 60 are rotated as one body.

Figure 5:
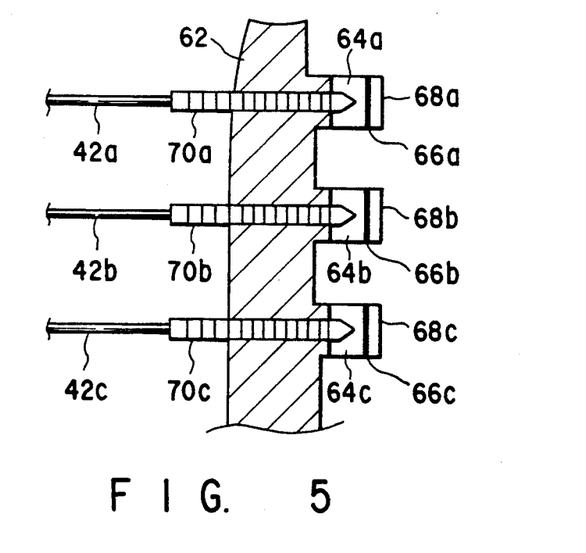
FIG. 5 is a cross-sectional view taken along line V—V in FIG. 4.

The cylindrical body 60, as shown in FIG. 5, comprises an insulating resin cylindrical member 62, an n-number of metal rings 64 arranged on the outer periphery of the cylindrical member 62 in parallel with intervals from one another, an n-number of adhesive double coated tapes or coupling means 66 made of a material such as silver with good electrical conductivity, an n-number of metal tapes 68 or strip members made of a material such as silver with good electrical conductivity, and an n-number of electrically conductive screws 70.

In the following description, the n-number of metal rings 64 are represented by three metal rings 64a, 64b and 64c the n-number of adhesive double coated tapes 66 by three adhesive double coated tapes 66a, 66b and 66c, the n-number of metal tapes 68 by three metal tapes 68a, 68b and 68c, and the n-number of electrically conductive screws 70 by three electrical conductive screws 70a, 70b and 70c.

The cylindrical body 60 is manufactured in a manner which will now be described. An insulating resin such as epoxy resin is molded into an annular body by a mold process. An n-number of grooves or striae, which are parallel along the axis of the annular body, are formed in the annular body by a cutting process, thus obtaining the insulating resin cylindrical body 62 having a plurality of striae arranged in parallel along its axial direction. That is, the grooves are annular, extending in the circumferential direction of the annular body. The n-number of metal rings 64 of an electrically conductive material such as brass are fitted on an n-number of ridges left between the grooves. The n-number of adhesive double coated tapes 66 are attached to the entire periphery of the n-metal rings 64. Further, the n-metal tapes 68 are attached to the entire periphery of the n-adhesive tapes 66. As is shown in FIG. 6, the mutually facing end faces of the beginning terminal portions 68S and ending terminal portions 68E of the metal tapes 68 are coated with epoxy resin-based adhesive, thereby preventing peeling. In addition, as is shown in FIG. 5, the n-screws 70 are inserted from the metal rings 64a, 64b and 64c, penetrating the insulating resin cylindrical member 62.

Figure 7:
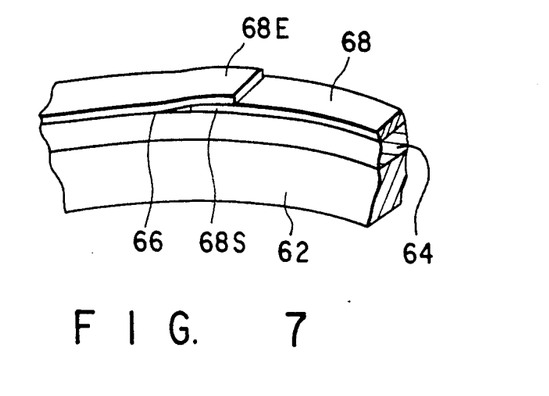
FIG. 7 is a view for explaining FIG. 5.

First end portions of an n-number of cables 42 are connected to the tip portions of the electrically conductive screws 70a, 70b and 70c, and second end portions thereof are connected to the x-ray tube 110. In the following description, the n-cables 42 are represented by three cables 42a, 42b and 43c. The ending terminal portions 68E of the metal tapes 68 are overlapped on the beginning terminal portions 68S, as shown in FIG. 7.

Figure 8:
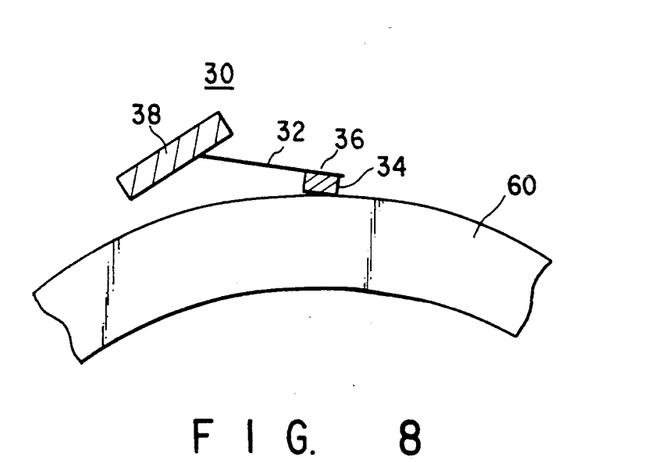
FIG. 8 is a schematic cross-sectional view of portion B in FIG. 4.

The brush unit 30, as shown in FIG. 8, comprises a block 38 and an n-number of brushes 36 constituted by an n-number of brush shanks 32 made of electrically conductive spring material and an n-number of contacts 34 made of a material such as silver with good electrical conductivity. First end portions of the brush shanks 32 are connected to the contacts 34, and second end portions thereof are fixed to the block 38. In the following description, the n-brushes 36 are represented by three brushes 36a, 36b and 36c.

While the cylindrical body 60 is being rotated, the brushes 36a, 36b and 37c are always put in contact with the metal rings 64a, 64b and 64c. The block 38 is connected to the low voltage power supply 114 via an n-number of cables 40. In the following description, the cables 40 are represented by three cables 40a, 40b and 40c. With the above structure, even when the cylindrical body 60 and the x-ray tube 110 are rotated continuously, electric power can easily be supplied from the low voltage power supply 114 to the x-ray tube 110 through the cables 40a, 40b and 40c, block 34, brushes 36a, 36b and 36c, metal rings 64a, 64b and 64c, electrically conductive screws 70a, 70b and 70c, and cables 42a, 42b and 42c.

According to this embodiment, only by attaching the electrically conductive metal tapes 68a, 68b and 68c to the metal rings 64a, 64b and 64c via electrically conductive adhesive double coated tapes 66a, 66b and 66c, the electrical conductivity and wear resistance are enhanced. Thereby, the efficiency in assembly of the cylindrical body 60 is enhanced, and the cost of the slip ring device 116 can be reduced.

Figure 9:
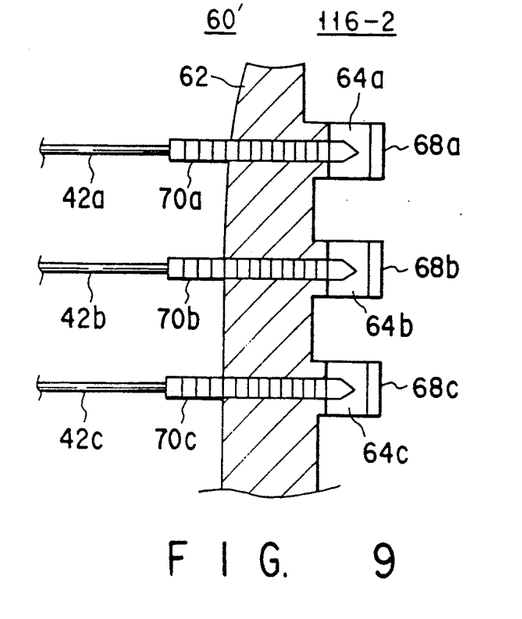
FIG. 9 is a cross-sectional view of a cylindrical body, for illustrating a slip ring device according to a second embodiment of the invention mounted in an x-ray CT scanner.

FIG. 9 is a perspective view of a low voltage slip ring device 116-2 according to a second embodiment of the invention. In a cylindrical body 60' according to the second embodiment, the electrically conductive adhesive double coated tapes 66 are omitted from the cylindrical body 60 of the first embodiment. Specifically, in the second embodiment, coupling means such as an adhesive is interposed between the metal tapes 68 and the metal rings 64. In this embodiment, the metal tapes 68 can be put in contact with the metal rings 64 by the coupling means with low contact resistance, and the tapes 68 can be firmly coupled to the rings 64.

Figure 10:
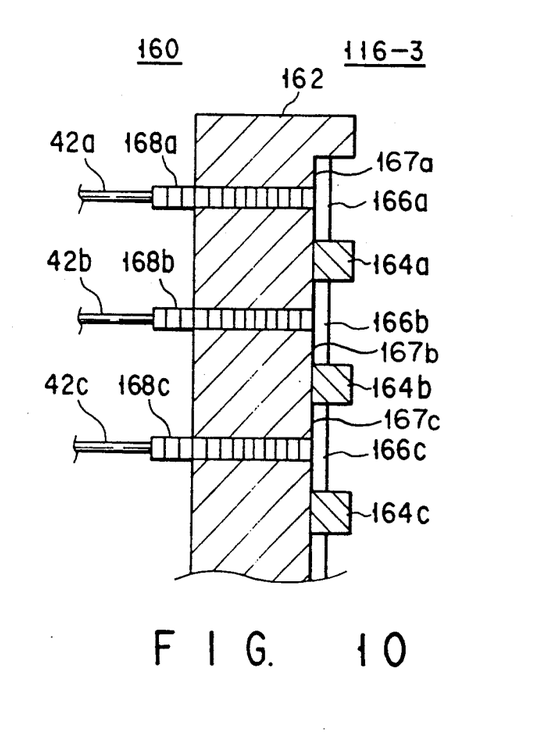
FIG. 10 is a cross-sectional view of a cylindrical body, for illustrating a slip ring device according to a third embodiment of the invention mounted in an x-ray CT scanner.

FIG. 10 is a perspective view showing a low pressure slip ring device 116-3 according to a third embodiment of the invention. The third embodiment differs from the preceding embodiments only with respect to a cylindrical body 160. The cylindrical body 160 of the third embodiment comprises an insulating resin cylindrical member 162, an n-number of barriers 164 of an insulating material such as rubber, which are arranged on the outer periphery of the cylindrical member 162 in parallel with intervals from one another, an n-number of metal tapes 166 of a material such as silver with high electrical conductivity, and an n-number of electrically conductive screws 168.

In the following description, the n-number of barriers 164 are represented by three rubber rings 164a, 164b and 164c, the n-number of metal tapes 166 by three metal tapes 166a, 166b and 166c, and the n-number of electrically conductive screws 168 by three screws 168a, 168b and 168c.

The cylindrical body with the above structure is manufactured by the following process. An insulating resin material such as epoxy resin is molded into an annular body by a mold process. The annular body is provided with a groove by a cutting process, thus obtaining the insulating resin cylindrical member 162. The groove is annular, extending in the circumferential direction of the annular body. The n-number of barriers 164 are fixed in the groove by means of an adhesive. The n-number of metal tapes 166 are attached around the entire groove between the barriers 164 by coupling means 167, such as the adhesive double coated tape described in detail above. The screws 168a, 168b and 168c are inserted from the metal tapes 166a, 166b and 166c through the insulating resin cylindrical member 162.

First end portions of an n-number of cables 42 are connected to the tip end portions of the electrically conductive screws 168a, 168b and 168c, and second end portions thereof are connected to the x-ray tube 110.

According to this embodiment, the metal rings and electrically conductive double coated tapes in the first and second embodiments may be omitted, and, only by attaching the electrically conductive metal tapes 166a, 166b and 166c to the electrically insulating resin cylindrical member 162, the electrical conductivity and wear resistance are enhanced. Thereby, the efficiency in assembly of the cylindrical body 160 is enhanced, and the cost of the slip ring device 116-3 can be reduced.

Figure 11:
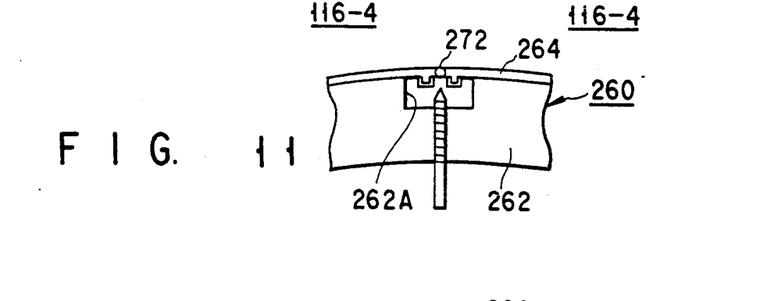
FIG. 11 is a partial cross-sectional view of a cylindrical body.
Figure 12:
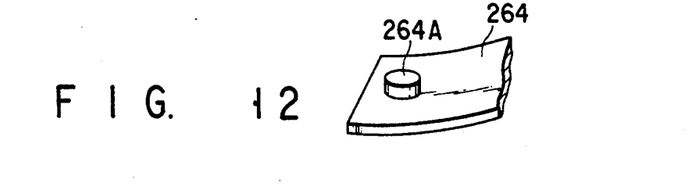
FIG. 12 is a perspective view of an end portion of a tape.
Figure 13:
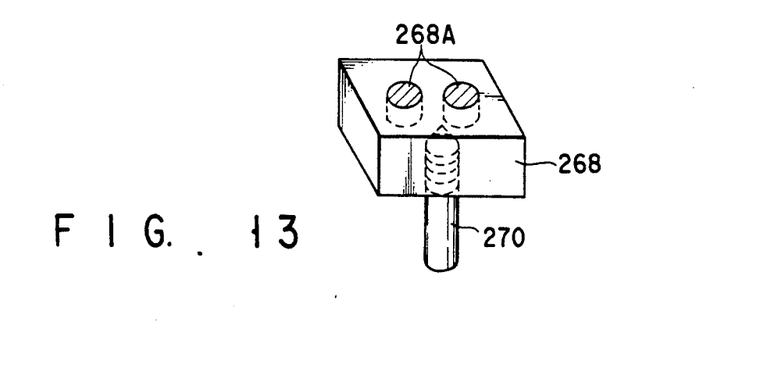
FIG. 13 is a perspective view of a brass block.

FIGS. 11 to 13 are perspective views showing a low voltage slip ring device 116-4 according to a fourth embodiment of the invention. The fourth embodiment differs from the third embodiment, with respect to the manner of attaching metal tapes 264 to a cylindrical body 260. As is shown in FIG. 11, the cylindrical body 260 of the fourth embodiment comprises an insulating resin cylindrical member 262 having holes 262A in the circumferential direction, an n-number of barriers (not shown) of an insulating material such as rubber, which are arranged on the outer periphery of the cylindrical member 262 in parallel with intervals from one another, an n-number of metal tapes 264 of a material such as silver with good electrical conductivity, and an n-number of lead members 266.

Each metal tape 264, as shown in FIG. 12, has projections 264A of an electrically conductive material at end portions on that side surface which is adhered to the insulating resin cylindrical member 262. On the other hand, each lead member 266, as shown in FIG. 13, comprises a block 268 of an electrically conductive material having holes 268A, and an electrically conductive screw 270 having a tip end portion inserted in the block 268. The block 268 is fitted in the hole 262A in the insulating resin cylindrical member 262. The screw 270 is exposed on the inside of the cylindrical member 262. The metal tape 264 is attached to the outer periphery of the cylindrical member 262, with its projections 264A fitted in the holes 268A of the block 268. The beginning portion and ending portion of the metal tape 264 are coupled by solder 272.

As has been described above, according to this embodiment, only by attaching the electrically conductive metal tapes 264 directly to the insulating resin cylindrical member 262, the electrical conductivity and wear resistance are enhanced. Thereby, the efficiency in assembly of the cylindrical body 260 is enhanced, and the cost of the slip ring device 116-4 can be reduced.

Figure 14:
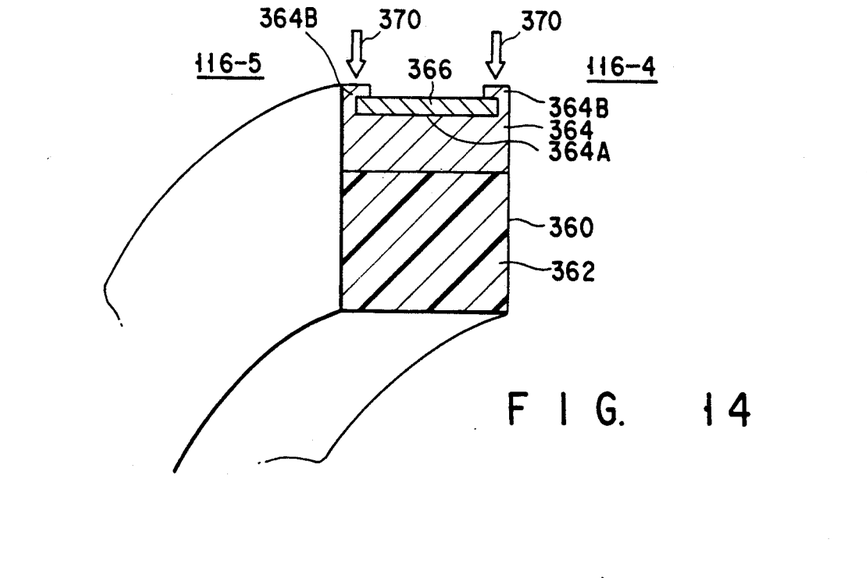
FIG. 14 is a partial cross-sectional view showing a slip ring device according to a fifth embodiment of the present invention mounted in an x-ray CT scanner.

FIG. 14 is a perspective view showing a low voltage slip ring device 116-5 according to a fifth embodiment of the invention. The fifth embodiment differs from the preceding embodiments only with respect to a cylindrical body 360. The cylindrical body 360 of the fifth embodiment, as shown in FIG. 14, comprises an insulating resin cylindrical member 362, an n-number of metal rings 364 arranged on the outer periphery of the cylindrical member 362 in parallel with intervals from one another, an n-number of metal tapes 366 of a material such as silver with good electrical conductivity, and an n-number of electrically conductive screws (not shown). The metal ring 364 has a groove 364A for grounding the metal tape 366 and clamp portions 364B on both sides of the groove 364A. Accordingly, the metal ring 364 has a C-cross section. The metal tape 366 is adhered to the groove 364A of the metal tape 366. Pressure is applied to the clamp portions 364B in the direction of arrow 370 (shown in FIG. 14); thereby, the metal tape 366 is held by the clamp portions 364B. The arrangement of the electrically conductive screws (not shown) are the same as is shown in FIG. 10.

As has been described above, according to this embodiment, only by attaching the electrically conductive metal tapes 366 directly to the insulating resin cylindrical member 362, the electrical conductivity and wear resistance are enhanced. Thereby, the efficiency in assembly of the cylindrical body 360 is enhanced, and the cost of the slip ring device 116-5 can be reduced.

The above embodiments are those of the low voltage slip ring device shown in FIG. 3. Of course, the structures shown in FIGS. 4 to 14 are applicable to the high voltage slip ring device shown in FIG. 3.

In addition, in the above embodiments, the present invention has been applied to the slip ring device mounted in the x-ray CT scanner; however, this invention is applicable to rotary electric machines such as an electric motor and a generator.

The present invention can provide the slip ring device wherein, only by attaching the electrically conductive metal tapes to the insulating resin cylindrical member, the electrical conductivity and wear resistance are enhanced, resulting in high efficiency in assembly of the cylindrical body, and low cost of the slip ring device.

Additional advantages and modifications will readily occur to those skilled in the art. Therefore, the invention in its broader aspects is not limited to the specific details, and representative devices shown and described herein. Accordingly, various modifications may be made without departing from the spirit or scope of the general inventive concept as defined by the appended claims and their equivalents.

What is claimed is:

1. A slip ring device comprising:
   a cylindrical body of an insulating material;
   at least one ring of an electrically conductive material fitted on the outer periphery of the cylindrical body;
   at least one strip member of an electrically conductive material arranged on the outer periphery of the ring;
   coupling means, situated between the strip member and the outer periphery of the ring, for electrically coupling the strip member and the outer periphery of the ring;
   at least one lead member of an electrically conductive material, having one end portion electrically connected to the ring and the other end portion led out of the inner periphery of the cylindrical body; and
   a brush unit of an electrically conductive material, situated in electrical contact with the strip member.

2. A slip ring device comprising:
   a cylindrical body of an insulating material;
   at least one ring of an electrically conductive material fitted on the outer periphery of the cylindrical body;
   at least one strip member of an electrically conductive material arranged on the outer periphery of the ring;
   at least one lead member of an electrically conductive material, having one end portion electrically connected to the ring and the other end portion led out of the inner periphery of the cylindrical body; and
   a brush unit of an electrically conductive material, situated in electrical contact with the strip member.

3. The slip ring device according to claim 1 or 2, wherein said cylindrical body has a plurality of striae arranged in parallel along the axial direction of the cylindrical body, and each of said at least one ring is fitted in a corresponding one of the striae.

4. The slip ring device according to claim 1, wherein said coupling means comprises an adhesive double coated tape formed of, as a main component, a tape-shaped electrically conductive material.

5. The slip ring device according to claim 1 or 2, wherein said brush unit comprises a brush constituted essentially by a contact made of an electrically conductive material fixed to an end portion of a brush shank made of an electrically conductive spring material, and a block for supporting the brush.

6. The slip ring device according to claim 5, wherein said cylindrical body is fixed to a rotor of an x-ray CT scanner, said block is provided on a stator of the x-ray CT scanner, electric power is supplied from a power supply to the lead member, and the brush unit is connected to an x-ray tube.

7. The slip ring device according to claim 6, wherein a sealed space formed between the rotor and the stator of the x-ray CT scanner contains said cylindrical body, said ring, said strip member, said coupling means, said lead member and said brush unit.

8. The slip ring device according to claim 1 or 2, wherein said strip member is made of silver.

9. The slip ring device according to claim 4, wherein the main component of said coupling means is silver.

10. The slip ring device according to claim 1 or 2, wherein said ring has a C-cross section with a groove extending in the longitudinal direction of the ring, said strip member is placed in the groove, and said strip member is brought into pressure contact with opposite side portions of the ring.

11. The slip ring device according to claim 1 or 2, wherein said cylindrical body is made of epoxy resin.

12. The slip ring device according to claim 1 or 2, wherein said cylindrical body is obtained by molding an epoxy resin by a mold process.

13. A slip ring device comprising:
   a cylindrical body of an insulating material;
   at least one strip member of an electrically conductive material arranged on the outer periphery of the cylindrical body;
   coupling means, situated between the strip member and the outer periphery of the cylindrical body, for electrically coupling the strip member and the outer periphery of the cylindrical body;
   at least one lead member of an electrically conductive material, having one end portion electrically connected to the strip member and the other end portion led out of the inner periphery of the cylindrical body; and
   a brush unit of an electrically conductive material, situated in electrical contact with the strip member.

14. The slip ring device according to claim 13, wherein said cylindrical body has a plurality of barriers arranged in parallel along the axial direction of the cylindrical body, and each of said at least one strip member is fitted in intervals between the plurality of barriers.

15. The slip ring device according to claim 13, wherein said brush unit comprises a brush constituted essentially by a contact made of an electrically conductive material fixed to an end portion of a brush shank made of an electrically conductive spring material, and a block for supporting the brush.

16. The slip ring device according to claim 15, wherein said cylindrical body is fixed to a rotor of an x-ray CT scanner, said block is provided on a stator of the x-ray CT scanner, electric power is supplied from a power supply to the lead member, and the brush unit is connected to an x-ray tube.

17. The slip ring device according to claim 16, wherein a sealed space formed between the rotor and the stator of the x-ray CT canner contains said cylindrical body, said strip member, said coupling means, said lead member and said brush unit.

18. The slip ring device according to claim 13, wherein said strip member is made of silver.

19. The slip ring device according to claim 13, wherein said strip member has two opposite end portions with projections formed thereon; and said coupling means and said lead member are constituted essentially by a block of an electrically conductive material having holes for receiving said projections and a screw electrically connected to the block, respectively.

20. The slip ring device according to claim 13, wherein said cylindrical body is obtained by molding an epoxy resin by a mold process.

21. The slip ring device according to claim 13, wherein said coupling means comprises an adhesive double coated tape formed of, as a main component, a tape-shaped electrically conductive material.

* * * * *

UNITED STATES PATENT AND TRADEMARK OFFICE
CERTIFICATE OF CORRECTION

PATENT NO. : 5,224,138
DATED : June 29, 1993
INVENTOR(S) : Yoshiki Hirao et al.

It is certified that error appears in the above-indentified patent and that said Letters Patent is hereby corrected as shown below:

Claim 17, column 10, line 19, change "canner" to --scanner--.

Signed and Sealed this

Seventh Day of June, 1994

Attest:

BRUCE LEHMAN

Attesting Officer      Commissioner of Patents and Trademarks